United States Patent
Otani

(10) Patent No.: US 10,625,056 B2
(45) Date of Patent: Apr. 21, 2020

(54) COIL, GUIDE WIRE, AND COIL MANUFACTURING METHOD

(71) Applicant: TERUMO KABUSHIKI KAISHA, Shibuya-ku, Tokyo (JP)

(72) Inventor: Yasunao Otani, Fuji (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 111 days.

(21) Appl. No.: 14/862,844

(22) Filed: Sep. 23, 2015

(65) Prior Publication Data

US 2016/0074631 A1 Mar. 17, 2016

Related U.S. Application Data

(63) Continuation of application No. PCT/JP2013/059831, filed on Apr. 1, 2013.

(51) Int. Cl.
  *A61M 25/09* (2006.01)
  *B21F 3/02* (2006.01)

(52) U.S. Cl.
  CPC ........... *A61M 25/09* (2013.01); *B21F 3/02* (2013.01); *A61M 2025/09091* (2013.01); *A61M 2025/09108* (2013.01); *A61M 2025/09175* (2013.01)

(58) Field of Classification Search
  None
  See application file for complete search history.

(56) References Cited

U.S. PATENT DOCUMENTS

| | | | |
|---|---|---|---|
| 4,003,369 A | 1/1977 | Beilman et al. | |
| 5,797,857 A | 8/1998 | Obitsu | |
| 5,931,830 A | 8/1999 | Jacobsen et al. | |
| 6,805,676 B2 | 10/2004 | Klint | |
| 2005/0273021 A1 | 12/2005 | Burgermeister | |
| 2009/0112063 A1* | 4/2009 | Bakos ................ | A61B 1/00078 600/114 |

(Continued)

FOREIGN PATENT DOCUMENTS

| | | |
|---|---|---|
| EP | 1454588 A | 9/2004 |
| JP | 57-059519 A | 4/1982 |

(Continued)

OTHER PUBLICATIONS

Machine Translation of Japanese Patent Publication JP2011277392A.*

(Continued)

*Primary Examiner* — Sean P Dougherty
*Assistant Examiner* — Benjamin S Melhus
(74) *Attorney, Agent, or Firm* — Buchanan Ingersoll & Rooney PC

(57) ABSTRACT

A coil is made by helically winding a wire rod. A cross-sectional shape of the wire rod of the coil includes a curved portion that is arcuately curved toward a center axis of the coil; a flat portion that is provided on an outer circumference of the coil, and is formed in a flat shape with a curvature that is smaller than a curvature of the curved portion; and at least one protruding portion that is provided at the boundary between the curved portion and the flat portion or in the vicinity of the boundary, and protrudes toward an adjacent wire rod.

11 Claims, 5 Drawing Sheets

(56) References Cited

U.S. PATENT DOCUMENTS

| | | | | |
|---|---|---|---|---|
| 2009/0198103 A1* | 8/2009 | Suzuki | ............ | A61B 17/00234 600/139 |
| 2010/0168619 A1 | 7/2010 | Elsesser | | |
| 2012/0078187 A1* | 3/2012 | Delap | ................ | A61M 25/005 604/171 |
| 2013/0190560 A1* | 7/2013 | Kaneko | ................ | A61B 1/0011 600/104 |

FOREIGN PATENT DOCUMENTS

| JP | 9-294812 A | 11/1997 |
|---|---|---|
| JP | 10-043306 A | 2/1998 |
| JP | 10-146390 A | 6/1998 |
| JP | 2002-539901 A1 | 11/2002 |
| JP | 2004261463 A | 9/2004 |
| JP | 2004-533271 A | 11/2004 |
| JP | 2005-125101 A | 5/2005 |
| JP | 20060247148 A | 9/2006 |
| JP | 2011-120739 A1 | 6/2011 |
| JP | 2011-177392 A | 9/2011 |
| WO | 0057944 A1 | 10/2000 |

OTHER PUBLICATIONS

International Search Report (PCT/ISA/210) dated Jun. 18, 2013, by the Japanese Patent Office as the International Searching Authority for International Application No. PCT/JP2013/059831.

The extended European Search Report dated Nov. 8, 2016, by the European Patent Office in corresponding European Patent Application No. 138808831-1501. (7 pgs).

Notice of Reasons for Rejection dated Jun. 21, 2016 issued in the corresponding Japanese Patent Application No. 2015-509628 and English translation (6 pages).

* cited by examiner

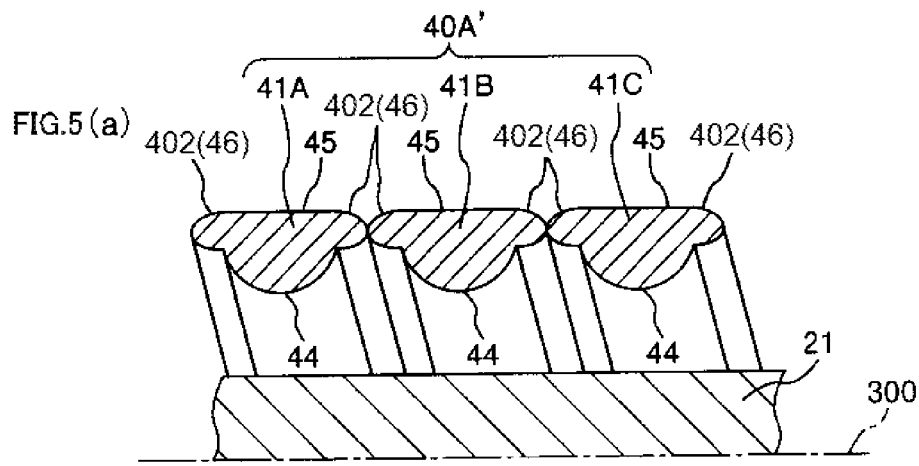
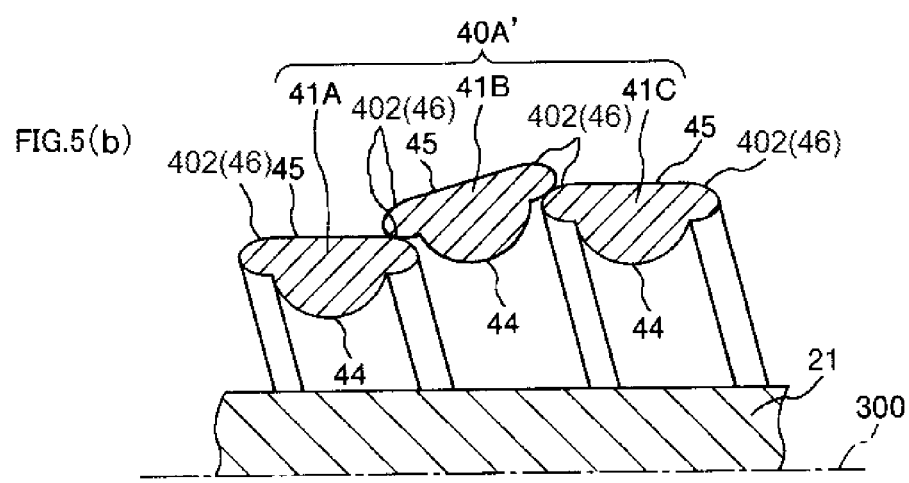
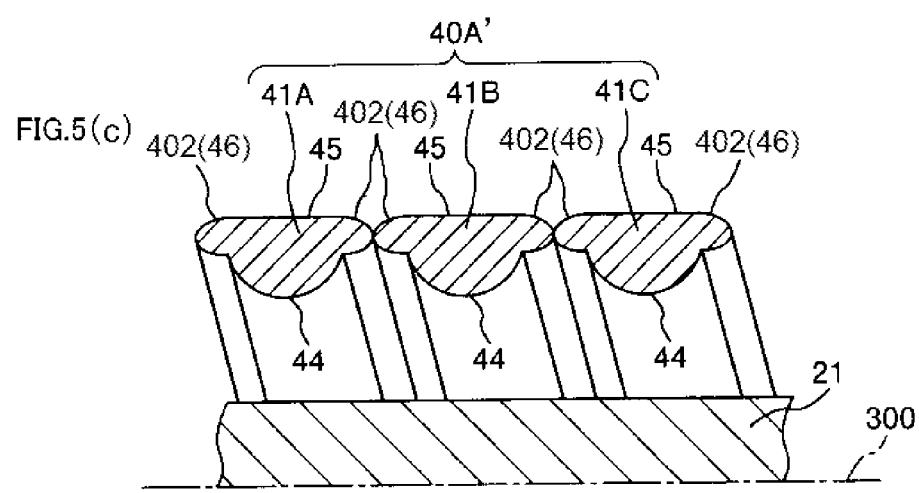

COIL, GUIDE WIRE, AND COIL MANUFACTURING METHOD

CROSS-REFERENCES TO RELATED APPLICATIONS

This application is a continuation of International Application No. PCT/JP2013/059831 filed on Apr. 1, 2013, the entire content of which is incorporated herein by reference.

TECHNICAL FIELD

The present invention relates to a coil, a guide wire, and a method of manufacturing the coil.

BACKGROUND DISCUSSION

A guide wire is used to guide a catheter which is used in the treatment of a portion on which it is difficult to perform surgery, in minimal invasive treatment for a human body, in cardioangiographic examination, or the like. When percutaneous coronary intervention (PCI) or the like is performed, a guide wire along with a balloon catheter under X-ray fluoroscopy is inserted into the vicinity of a stenotic portion of a coronary artery, that is, a target portion, while a distal end of the guide wire protrudes further than a distal end of the balloon catheter, and a distal end portion of the balloon catheter is guided to the vicinity of a stenosis.

JP-A-10-146390 discloses a guide wire that is used in this type of treatment. This guide wire is configured to include a wire main body (core member) that has flexibility; a coil (X-ray imaging metal coil) that is installed so as to cover an outer circumference of a distal end portion of the wire main body, and is made by winding a wire rod with a semicircular cross section; and coating layers (coating member made of synthetic resin, and a hydrophilic lubricating layer) that cover the outermost surfaces of the wire main body and the coil.

When the guide wire disclosed in JP-A-10-146390 is operated as described above, phenomena to be described hereinbelow may occur depending on a state of the coronary artery, for example, the degree of curving.

When the coil of the guide wire reaches (is inserted into) a steeply curved portion of the coronary artery, if the guide wire is pushed, an excessive force (which causes plastic deformation of the coil) is applied to the coil. In this case, a portion of the wire of the coil moves upward relative to the adjacent wire, and the coil undergoes plastic deformation. Since the wire rod of the coil has a semicircular cross section, a corner of the wire rod is stuck to the adjacent wire rod. For this reason, the coil does not return to a typical (normal) state, and a pushing force is not reliably transmitted to the distal end portion of the wire main body from a proximal end portion of the wire main body via the coil, that is, pushing performance is considerably decreased.

In a case where the plastic deformation of the coil occurs, the guide wire bulges (the outer diameter increases) due to the plastic deformation, and thus even the hydrophilic lubricating layer is provided on the coil of the guide wire that is disclosed in JP-A-10-146390; the catheter cannot be inserted due to the thickness of the guide wire.

In addition, in a case where the guide wire bulges as described above, when the coil of the guide wire reaches (is inserted into) the steeply curved portion of the coronary artery or the like, relatively large friction resistance may occur between the hydrophilic lubricating layer and the curved portion. For this reason, torque may not be reliably transmitted to the distal end portion of the wire main body from the proximal end portion of the wire main body via the coil, that is, torque transmission performance is considerably decreased, and the coil is ruptured due to an increase in the friction resistance.

SUMMARY

An object of the present disclosure is to solve these and other problems, and to provide a coil and a guide wire with good operability, and a coil manufacturing method.

A coil that is made by helically winding a wire rod, in which a cross-sectional shape of the wire rod includes: a curved portion that is arcuately curved toward a center axis of the coil; a flat portion that is provided on an outer circumference of the coil, and is formed in a flat shape with a curvature that is smaller than that of the curved portion; and at least one protruding portion that is provided at the boundary between the curved portion and the flat portion or in the vicinity of the boundary, and protrudes toward an adjacent wire rod.

In an embodiment, the outer surface of the protruding portion is curved, and the curvature of the outer surface is greater than that of the curved portion.

In an embodiment, in a no-load state in which an external force is not applied, the protruding portion is in contact with the adjacent wire rod.

In an embodiment, when an external force is applied such that contact pressure between the adjacent wire rods increases, one wire rod of the adjacent wire rods moves upward relative to the other wire rod, and when the external force is reduced or released, due to the resilience of the one wire rod, the one wire rod returns to an original position thereof while the curved portion of the one wire rod slides against the protruding portion of the other wire rod.

In an embodiment, the protruding portions are respectively provided at the boundaries or in the vicinity of the boundaries between the curved portions and the flat portions on both ends.

A guide wire includes a coil according to any one of the foregoing embodiments; and a wire main body that has flexibility, in which the wire main body is inserted into the coil.

There is provided a coil manufacturing method for manufacturing a coil according to any one of the foregoing embodiments, in which an outer circumferential surface of a coil member, which is made by helically winding a linear base material with a circular cross section, is ground or cut in such a way that a burr working as the protruding portion is formed, and is formed in a flat shape with a curvature which is smaller than that of the curved portion.

In an embodiment of the coil manufacturing method, when the coil member is ground or cut, the coil member rotates around a center axis of the coil.

In an embodiment of the coil manufacturing method, when the coil member is ground or cut, the coil member moves along the center axis of the coil.

In an embodiment of the coil manufacturing method, the coil member is ground by a circular column-shaped or circular disk-shaped grinding stone.

In an embodiment of the coil manufacturing method, when the coil member is ground or cut, the grinding stone rotates around the center axis of the grinding stone, and moves along the center axis of the coil.

In an embodiment of the coil manufacturing method, the burr is formed in a forward movement direction of the grinding stone.

According to the present disclosure, it is possible to reliably prevent the adjacent wire rods from being stuck to each other, and to prevent the occurrence of a state in which the adjacent wire rods move upward relative to each other and remain as it is, and to obtain the coil and the guide wire with good operability.

In particular, since the cross-sectional shape of the wire rod of the coil has the protruding portion that protrudes toward the adjacent wire rod, even if one wire rod of the adjacent wire rods moves upward relative to the other wire rod, the one wire rod can return to a no-load state while sliding against the protruding portion of the other wire rod. Accordingly, it is possible to prevent the guide wire from bulging, and to prevent an increase in friction resistance associated with the bulging of the guide wire, and it is possible to reliably transmit a pushing force and a rotating force to the distal end of the guide wire, that is, the operability of the guide wire is improved.

BRIEF DESCRIPTION OF THE DRAWINGS

FIGS. 5(a), 5(b) and 5(c) show longitudinal sectional views illustrating a deformation process of a guide wire (a coil) in a second embodiment.

DETAILED DESCRIPTION

Hereinafter, preferred embodiments of a coil and a guide wire will be described in detail with reference to the accompanying drawings.

First Embodiment

Figure 1:
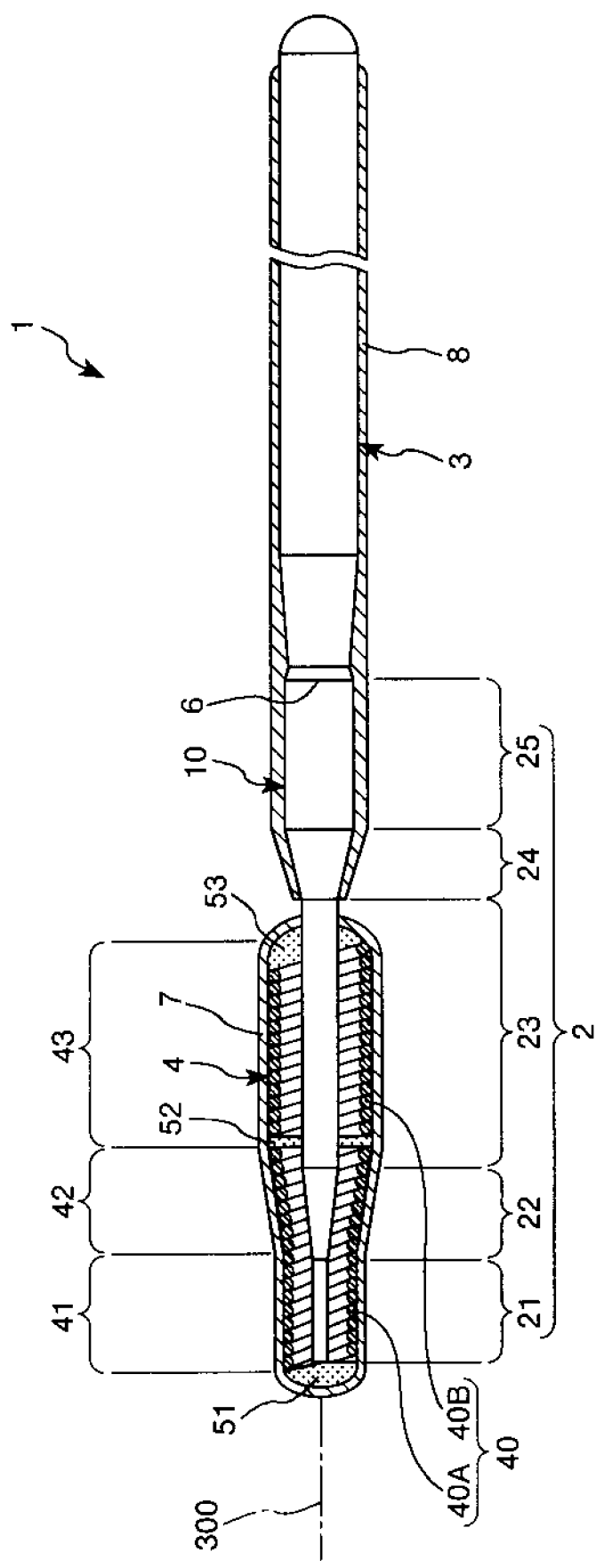
FIG. 1 is a partial longitudinal sectional view (schematic side view) of a guide wire (a coil) in a first embodiment.
Figure 2A:
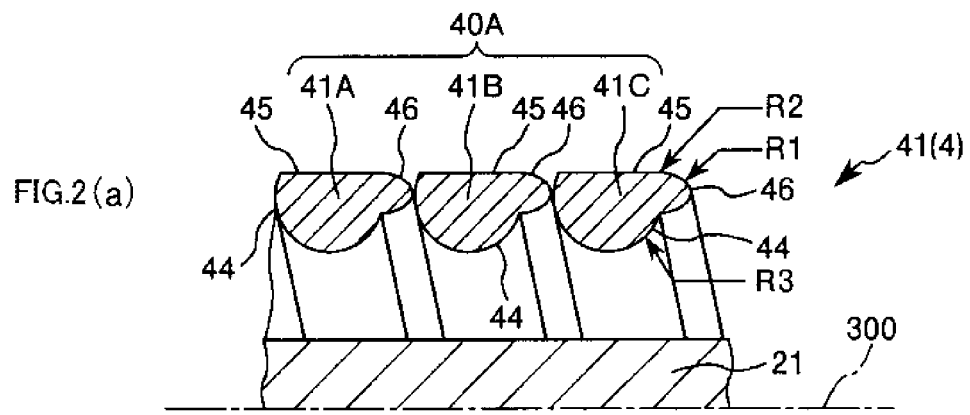
FIGS. 2(a), 2(b) and 2(c) show longitudinal sectional views illustrating a deformation process of the coil in FIG. 1.
Figure 2B:
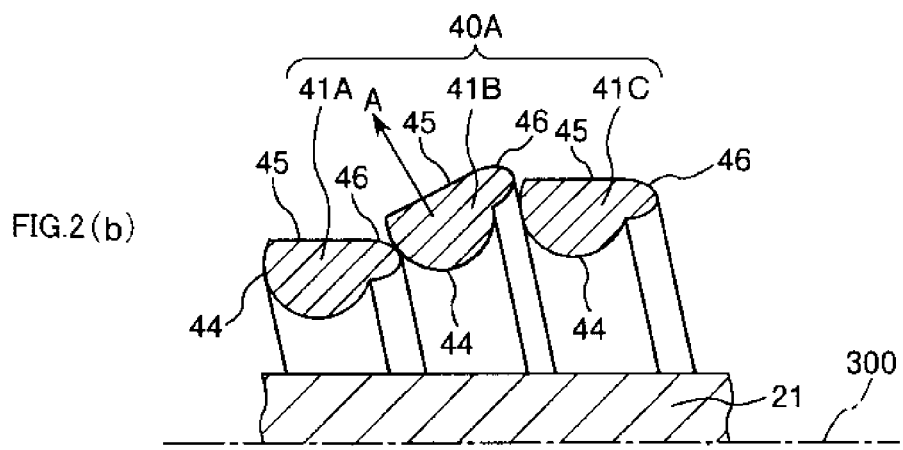
Figure 2C:
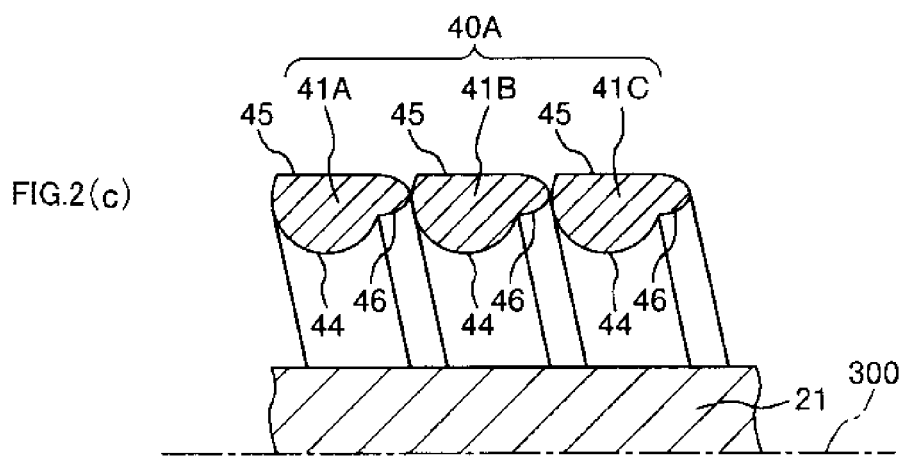
Figure 3:
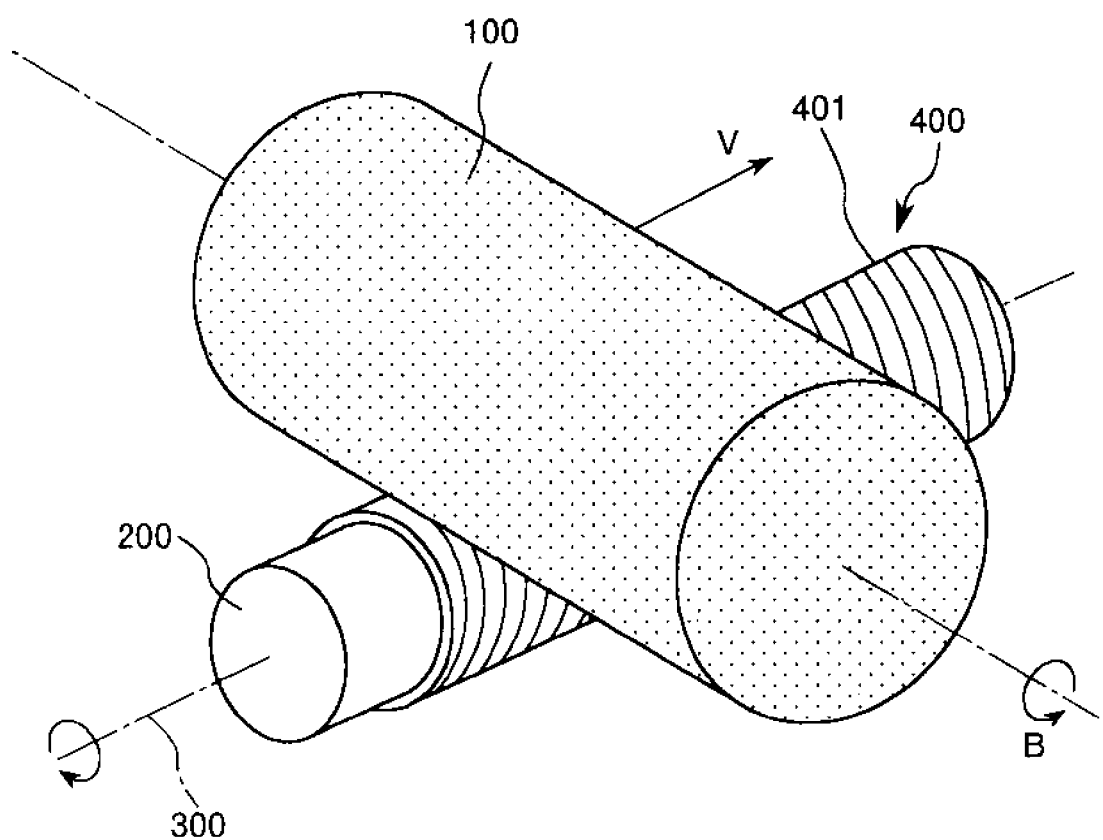
FIG. 3 is a view (perspective view) illustrating a method of manufacturing the coil in FIG. 1.
Figure 4A:
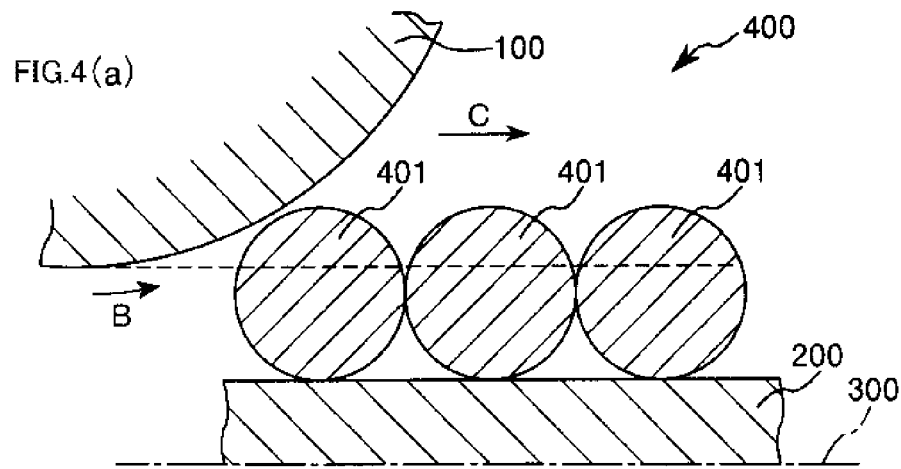
FIGS. 4(a), 4(b) and 4(c) show views (longitudinal sectional views) sequentially illustrating steps of manufacturing the coil in FIG. 1.
Figure 4B:
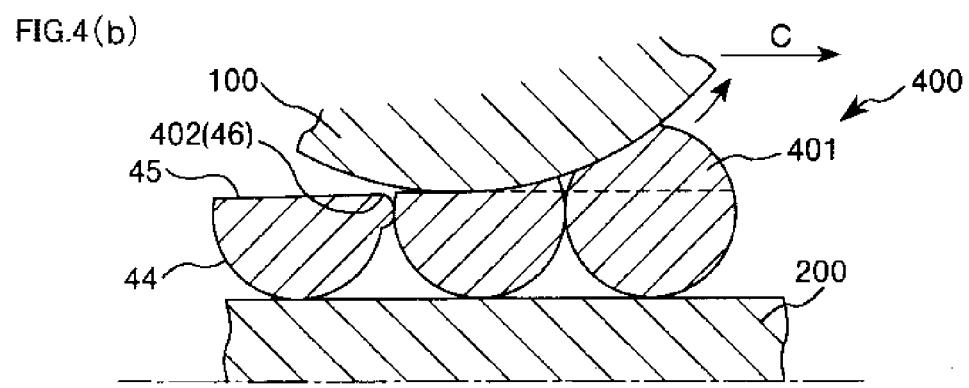
Figure 4C:
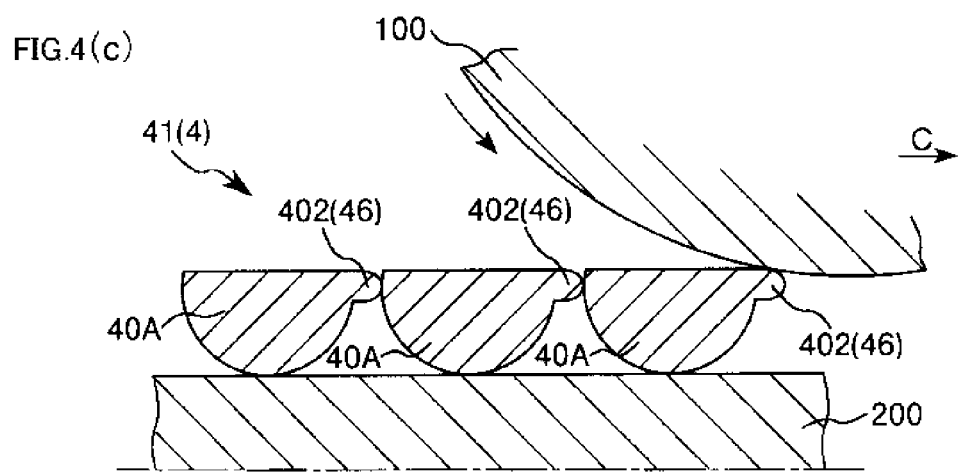

FIG. 1 is a partial longitudinal sectional view (schematic side view) of a guide wire (a coil) in a first embodiment, FIG. 2 shows longitudinal sectional views illustrating a deformation process of the coil in FIG. 1, FIG. 3 is a view (perspective view) illustrating a method of manufacturing the coil in FIG. 1, and FIG. 4 shows views (longitudinal sectional views) sequentially illustrating steps of manufacturing the coil in FIG. 1. Hereinafter, for illustrative purposes, in FIGS. 1, 2, and 4, the right side and the left side are respectively referred to as a "proximal end" and a "distal end", and an upper side and a lower side are respectively referred to as the "top" and the "bottom". In FIGS. 1 to 4, for ease of understanding, the coil and the guide wire are schematically illustrated in a state where the longitudinal length of each of the coil and the guide wire is reduced, and the radial length (thickness) of each of the coil and the guide wire is increased, and the ratio of the longitudinal length to the radial length is different from an actual ratio (the same also applies to FIG. 5).

A guide wire 1 illustrated in FIG. 1 is a guide wire for a catheter (or an endoscope) which is used while being inserted into the bore of a catheter, and has a flexible wire main body 10 in which a second wire 3 disposed on a proximal end side of a first wire 2 is joined (connected) to the first wire 2 that is disposed on a distal end side; and a helical coil 4. The entire length of the guide wire 1 is not limited to a specific dimension, and the guide wire 1 preferably has a total length of approximately 200 mm to 5000 mm. The outer diameter of the guide wire 1 is not limited to a specific dimension, and typically, the guide wire 1 has an outer diameter of approximately 0.2 mm to 1.2 mm.

The first wire 2 is made of a wire rod (core member) with flexibility or elasticity. The length of the first wire 2 is not limited to a specific dimension, and the first wire 2 preferably has a length of approximately 20 mm to 1000 mm.

In the embodiment, the first wire 2 has a portion (constant outer-diameter portion) that has a constant outer diameter, and a tapered portion (gradual outer-diameter reduction portion), the outer diameter of which gradually decreases toward a distal end thereof. In a configuration which is illustrated, the first wire 2 has a constant outer-diameter portion 25; a tapered portion 24; a constant outer-diameter portion 23 with an outer diameter which is smaller than that of the constant outer-diameter portion 25; a tapered portion (main body-side tapered portion) 22; and a foremost end portion 21, all of which are sequentially disposed from a proximal end side to a distal end side.

Since the guide wire 1 has the tapered portions 22 and 24, it is possible to gradually decrease the rigidity (flexural rigidity, torsional rigidity) of the first wire 2 toward the proximal end. As a result, a distal end portion of the guide wire 1 can have good flexibility, the guide wire 1 can have an improved ability of being able to follow a body lumen (body cavity) such as a blood vessel or the like, and improved safety, and can be prevented from being bent, for example.

The taper angle (reduction rate in the outer diameter) of each of the tapered portions 22 and 24 may be constant or be changed along a longitudinal direction (hereinafter, which is simply referred to as a "longitudinal direction") of the wire main body 10. For example, regions formed with a relatively large taper angle (reduction rate in the outer diameter) and regions formed with a relatively small taper angle may be alternately repeated multiple times.

For example, the foremost end portion 21 can be configured as a constant outer-diameter portion that has an outer diameter which is smaller than that of the constant outer-diameter portion 23.

For example, the foremost end portion 21 is formed in the shape of a flat plate (ribbon shape), and it is possible to use the foremost end portion 21 in a state where the shape of the foremost end portion 21 is changed (re-shaped or shaped) to a desired shape. Typically, a doctor uses the guide wire in a state where the distal end portion of the guide wire is bent in a predetermined desired shape so that a distal end portion of a guiding catheter or the like can be adapted to the shape of a blood vessel, or can be smoothly guided to a blood vessel branch. As such, the bending of the distal end portion of the guide wire in a desired shape is referred to as the term "re-shaping". Since the foremost end portion 21 is provided, it is possible to easily and reliably re-shape the guide wire 1, and to considerably improve operability when the guide wire 1 is inserted into a living body.

The length of the foremost end portion 21 is not limited to a specific dimension, and the foremost end portion preferably has a length of approximately 5 mm to approximately 200 mm, and more preferably has a length of approximately 10 mm to approximately 150 mm. In particular, in a case where the foremost end portion 21 is re-shaped and then is used, when the length of the foremost end portion 21 is excessively long, operability of the guide wire 1 deteriorates due to the material of the foremost end portion 21, and when the length of the foremost end portion 21 is excessively short, the distal end portion of the guide wire 1 cannot be formed in a desired shape.

The material (wire) of the first wire 2 is not limited to a specific material, for example, various metal materials such as an Ni—Ti alloy, stainless steel or the like can be used as the material of the first wire 2, and preferably, alloys with pseudoelasticity (including a superelastic alloy) are used. A superelastic alloy is more preferably used. Since the first wire 2 is made of the superelastic alloy which is relatively flexible, has resilience, and is unlikely to have a tendency to bend, the distal end portion of the guide wire 1 can have sufficient flexibility, and resilience against bending. Therefore, it is possible to obtain an improved ability of being able to follow complex curved and bent blood vessels or the like, and to obtain better operability. Since the first wire 2 is unlikely to have a tendency to bend due to the resilience of the first wire 2, even if the first wire 2 repeatedly undergoes curving and bending deformation, the tendency to bend of the first wire 2 of the guide wire 1 in use can be prevented from causing deterioration in the operability.

The pseudoelastic alloys includes pseudoelastic alloys with any tensile stress-strain curves, pseudoelastic alloys in which the transformation point of As, Af, Ms, Mf, or the like can be or cannot be measured distinguishing manner, and anelasitc alloys which are considerably deformed (distorted) due to stress, and substantially return to their original shape when the stress is removed.

With regard to the compositions of the superelastic alloys exemplified herein, preferably, a Ni—Ti alloy such as a Ni—Ti alloy containing 49% to 52% of Ni atoms, or the like, a Cu—Zn alloy containing 38.5% to 41.5% by weight of Zn, a Cu—Zn—X alloy containing 1% to 10% by weight of X (X is at least one type of Be, Si, Sn, Al, and Ga), a Ni—Al alloy containing 36% to 38% of Al atoms, and the like can be used. In particular, the Ni—Ti alloy among these alloys is preferably used. The superelastic Ni—Ti alloy has good adhesion to a resin coating layer 8 (to be described later) or the like.

A distal end of the second wire 3 is joined (connected) to a proximal end of the first wire 2 (proximal end of the constant outer-diameter portion 25). The second wire 3 is made of a wire rod (core member) with flexibility or elasticity. The length of the second wire 3 is not limited to a specific dimension, and the second wire 3 preferably has a length of approximately 20 mm to 4800 mm, and more preferably has a length of approximately 1400 mm to 3000 mm.

The mean outer diameter of the second wire 3 is greater than that of the first wire 2. Accordingly, since the guide wire 1 is configured such that the first wire 2 on the distal end side of the guide wire 1 has good flexibility, and the second wire 3 on the proximal end side thereof has high rigidity, the flexibility of the distal end portion can be compatible with good operability (pushing performance, torque transmission performance, and the like).

A method of joining the first wire 2 to the second wire 3 is not limited to a specific method, and, for example, it is possible to use various methods such as welding, soldering or the like. The first wire 2 is preferably joined to the second wire 3 using welding.

The welding method is not limited to a specific method, and for example, friction pressure welding, spot welding using a laser beam, butt resistance welding such as upset welding, or the like can be used. In particular, the butt resistance welding is preferably used because it is possible to relatively simply obtain high joining strength.

The second wire 3 is made of a material what is different from that of the first wire 2, and particularly, the second wire 3 is preferably made of a material, the elastic modulus (Young's modulus (modulus of longitudinal elasticity), modulus of rigidity (modulus of transverse elasticity), or bulk modulus) of which is higher than that of the first wire 2. Accordingly, the second wire 3 can have appropriate rigidity (flexural rigidity and torsional rigidity), and the guide wire 1 is rigid, and as a result, it is possible to obtain improved pushing performance and torque transmission performance, and to obtain better ease of insertion.

The material (wire) of the second wire 3 is not limited to a specific material insofar as the material of the second wire 3 is different from that of the first wire 2, and it is possible to use various metal materials such as stainless steel (for example, all types of SUS such as SUS304, SUS303, SUS316, SUS316L, SUS316J1, SUS316J1L, SUS405, SUS430, SUS434, SUS444, SUS429, SUS430F, SUS302, or the like), piano wire, cobalt alloys, alloys with pseudoelasticity, and the like. Stainless steel or a cobalt alloy is preferably used as the material of the second wire 3, and stainless steel is more preferably used. Since the second wire 3 is made of stainless steel or a cobalt alloy, the guide wire 1 can have good pushing performance and torque transmission performance.

In the embodiment, the wire main body 10 is configured such that the first wire 2 is joined to the second wire 3; however, the present invention is not limited to that configuration in the embodiment, and for example, the wire main body 10 may be configured as a single continuous wire rod.

The coil 4 is installed on an outer circumference of the distal end portion of the wire main body 10, that is, on outer circumferences of the foremost end portion 21, the tapered portion 22, and the constant outer-diameter portion 23 of the first wire 2. The coil 4 is a member that is made by helically winding a wire rod 40, and is installed in such a way as to cover the distal end portion of the wire main body 10, that is, the foremost end portion 21, the tapered portion 22, and a portion of the constant outer-diameter portion 23 (a large portion of the constant outer-diameter portion 23) excluding a proximal end portion of the constant outer-diameter portion 23 in the first wire 2. The first wire 2 is inserted into a substantially inner center portion of the coil 4.

As illustrated in FIG. 1, the coil 4 corresponds to the foremost end portion 21, the tapered portion 22, and the constant outer-diameter portion 23 of the first wire 2, and has a portion (constant outer-diameter/inner-diameter portion), the outer diameter and the inner diameter of which are constant, and a tapered portion (gradual outer-diameter/inner-diameter reduction portion), the outer diameter and the inner diameter of which gradually decrease toward the distal end. In an illustrated configuration, the coil 4 has the following portions which are sequentially disposed from the proximal end side to the distal end side: a constant outer-diameter/inner-diameter portion 43; a tapered portion 42; and a constant outer-diameter/inner-diameter portion (constant inner-diameter portion) 41, an outer diameter and an inner diameter of which are smaller than those of the constant outer-diameter/inner-diameter portion 43. The constant outer-diameter/inner-diameter portion 43, the tapered portion 42, and the constant outer-diameter/inner-diameter portion 41 are positioned in such a way as to respectively correspond to the constant outer-diameter portion 23, the tapered portion 22, and the foremost end portion 21 of the first wire 2. In the distal end portion of the wire main body 10, the distance between the outer surface of the wire main body (core member) 10 and the inner surface of the coil 4 is substantially constant along the longitudinal direction.

Since the first wire 2 and the coil 4 are coaxially disposed, the distal end portion of the wire main body 10 can be non-eccentrically deformed.

In all of the constant outer-diameter/inner-diameter portion 43, the tapered portion 42, and the constant outer-diameter/inner-diameter portion 41 of the coil 4, two adjacent wire rods 40 are in contact with each other in a no-load state in which an external force is not applied. That is, the wire rods 40 are densely disposed without a gap therebetween.

The wire rod 40 can be divided into a wire rod 40A that is positioned on the distal end side, and a wire rod 40B that is positioned closer to the proximal end side than the wire rod 40A (refer to FIG. 1). The wire rod 40B has a circular cross section, and forms the constant outer-diameter/inner-diameter portion 43 and the tapered portion 42 of the coil 4.

In contrast, the wire rod 40A has a substantially semicircular cross section which has a curved surface close to a center axis 300 of the coil 4, and forms the constant outer-diameter/inner-diameter portion 41 of the coil 4. Accordingly, it is possible to decrease the outer diameter of the constant outer-diameter/inner-diameter portion 41 without decreasing the inner diameter of the constant outer-diameter/inner-diameter portion 41. As a result, it is possible to decrease the diameter of the guide wire 1 while sufficiently ensuring the internal space of the coil 4, and thus it is possible to selectively set the shape and the size of the wire main body 10.

Hereinafter, the wire rod 40A will be described in detail. Hereinafter, for ease of understanding, a portion (portions in which the wire rod 40A is turned three times) of the constant outer-diameter/inner-diameter portion 41 will be described with reference to FIG. 2. The portions in which the wire rod 40A is turned three times are respectively referred to as a wire rod 41A, a wire rod 41B, and a wire rod 41C, which are sequentially positioned from the distal end side. Since the wire rods 41A, 41B, and 41C have the same configuration, hereinafter, the wire rod 41A will be representatively described.

The cross-sectional shape of the wire rod 41A has a curved portion 44, a flat portion 45, and a protruding portion 46.

The curved portion 44 is a portion that is provided close to the center axis 300, and is arcuately curved toward the center axis 300. A curvature R3 of the curved portion 44 preferably is a value of $15 \times 10^3$ to $5 \times 10^4$ $m^{-1}$, and more preferably is a value of $28 \times 10^3$ to $4 \times 10^4$ $m^{-1}$.

The flat portion 45 is positioned on the outer circumference of the coil 4, and is formed in a flat shape which has a curvature that is smaller than that of the curved portion 44. A curvature R2 of the flat portion 45 preferably is a value of 0 to $2 \times 10^4$ $m^{-1}$, and more preferably is a value of 0 to $4 \times 10^3$ $m^{-1}$. Accordingly, concavities and convexities of the outer circumferential surface of the constant outer-diameter/inner-diameter portion 41 are reduced. As a result, the outer surface of the constant outer-diameter/inner-diameter portion 41 becomes smooth, the diameter of the constant outer-diameter/inner-diameter portion 41 is reduced, and the guide wire 1 easily moves forward within a curved blood vessel.

The protruding portion 46 is provided at the proximal end-side boundary between the curved portion 44 and the flat portion 45, and protrudes toward the wire rod 41B that is positioned (adjacent) on the proximal end side. The outer surface of the protruding portion 46 is curved in a curvature that is greater than the curvature R3 of the curved portion 44. The protruding portion 46 is continuous with the flat portion 45, and the boundary between the flat portion 45 and the protruding portion 46 is smooth. In a no-load state, the protruding portion 46 is in contact with a distal end portion of the curved portion 44 of the wire rod 41A.

A curvature R1 of the protruding portion 46 preferably is a value of $3 \times 10^4$ to $2 \times 10^5$ $m^{-1}$, and more preferably is a value of $6 \times 10^4$ to $12 \times 10^4$ $m^{-1}$. The curvature R1 of the protruding portion 46 preferably is 10% to 70% of the curvature R3 of the curved portion 44, and more preferably is 30% to 40% of the curvature R3 of the curved portion 44.

A description to be given hereinafter relates to a case in which an external force (hereinafter, which is simply referred to as an "external force") is applied to the wire rod 40A such that contact pressure between the wire rod 41A and the wire rod 41B and between the wire rod 41B and the wire rod 41C increases.

When the guide wire 1 is pushed toward the distal end side in a living body, an external force is applied to the wire rod 40A. Accordingly, contact pressure between the protruding portion 46 of the wire rod 41A and the curved portion 44 of the wire rod 41B increases, and contact pressure between the protruding portion 46 of the wire rod 41B and the curved portion 44 of the wire rod 41C increases. When this external force is large enough that the positions of the wire rods 41A to 41C cannot be maintained, the wire rod 41B is expelled in a direction of arrow A in FIG. 2(b) by the wire rods 41A and 41C. At this time, the curved portion 44 of the wire rod 41B slides against the protruding portion 46 of the wire rod 41A, the protruding portion 46 of the wire rod 41B slides against the curved portion 44 of the wire rod 41C, and then the wire rod 41B moves upward relative to the wire rods 41A and 41C.

In this state, when the pushing of the guide wire 1 toward the distal end side is stopped, or is limited, and the external force is reduced or released, the contact pressure between the protruding portion 46 of the wire rod 41A and the curved portion 44 of the wire rod 41B decreases, and the contact pressure between the protruding portion 46 of the wire rod 41B and the curved portion 44 of the wire rod 41C decreases. Accordingly, the wire rod 41B returns to its original position (no-load state) due to a restoring force (elastic force) of the wire rod 41B. At this time, the curved portion 44 of the wire rod 41B slides against the protruding portion 46 of the wire rod 41A, the protruding portion 46 of the wire rod 41B slides against the flat portion 45 of the wire rod 41C, and then the wire rod 41B can return to an original state (refer to FIG. 2(c)).

In this way, even if the wire rod 41B moves upward relative to the wire rods 41A and 41C, the wire rod 41B can easily return the original state. Accordingly, it is possible to reliably prevent the wire rod 41B from undergoing plastic deformation in which the wire rod 41B moves upward relative to the wire rods 41A and 41C, and remains as it is. It is possible to reliably transmit a pushing force and a rotating force to the distal end of the guide wire 1. As a result, the guide wire 1 is good in operability.

The case, in which the wire rod 41B moves upward relative to the adjacent wire rods 41A and 41C, has been described; however, and even if the wire rod 41A or the wire rod 41C moves upward relative to the adjacent wire rod 41B, it is possible to obtain the aforementioned effects. In the embodiment, the protruding portion 46 protrudes toward the proximal end side; however, even if the protruding portion 46 protrudes toward the distal end side, it is possible to obtain the same effects.

The coil 4 is preferably made of a metal material. Stainless steel, superelastic alloys, cobalt alloys, noble metals such as gold, platinum, tungsten, or the like, alloys (for example, a platinum-iridium alloy) containing these noble metals, and the like can be used as the metal material of the coil 4. In particular, when the coil 4 is made of a radiopaque material such as noble metals, the guide wire 1 can be X-ray imaged, and it is possible to insert the guide wire 1 into the living body while confirming the position of the distal end portion under X-ray fluoroscopy, which is preferable. A distal end side and a proximal end side of the coil 4 may be made of different materials. For example, the distal end side of the coil may be made of a radiopaque material, and the proximal end side of the coil may be made of a material (stainless steel or the like) through X rays are relatively transmitted. The entire length of the coil 4 is not limited to a specific dimension, and the coil 4 preferably has a total length of approximately 5 mm to 500 mm.

A distal end portion and a proximal end portion of the coil 4 are fixed to the first wire 2 using fixing materials 51 and 53, respectively. An intermediate portion of the coil 4 is fixed to the first wire 2 using a fixing material 52. Solder (brazing material) is used as the fixing materials 51 to 53. The fixing materials 51 to 53 are not limited to solder, and may be adhesives. A method of fixing the coil 4 to the first wire 2 is not limited to the use of the aforementioned fixing materials, and may be welding. A distal end surface of the fixing material 51 is preferably rounded so as to prevent an inner wall of a body cavity such as a blood vessel or the like from being damaged.

In the embodiment, since the coil 4 is installed in this way, the distal end portion of the guide wire 1 can have appropriate flexibility, and since the first wire 2 is covered with the coil 4, and has a small contact area, it is possible to reduce slide resistance of the first wire 2, and the operability of the guide wire 1 is further improved.

The guide wire 1 has a resin coating layer 8 that entirely or partially covers the outer circumferential surface (outer surface) of the wire main body 10. In the illustrated configuration, the resin coating layer 8 is provided on the outer circumferences of the tapered portion 24, the constant outer-diameter portion 25 of the first wire 2, and the outer circumference of the second wire 3.

The resin coating layer 8 can be formed for various purposes, and for example, the friction (slide resistance) of the guide wire 1 is reduced, and sliding performance is improved, and thus the operability of the guide wire 1 is improved.

In order to reduce the friction (slide resistance) of the guide wire 1, the resin coating layer 8 is preferably made of friction reduction materials which will be described hereinbelow. Accordingly, friction resistance (slide resistance) between the guide wire 1 and the inner wall of the catheter in use therewith is reduced, and thus the sliding performance of the guide wire 1 is improved, and the operability of the guide wire 1 in the catheter is further improved. Since the slide resistance of the guide wire 1 is reduced, it is possible to more reliably prevent the occurrence of a kink (bending) or twist of the guide wire 1, and particularly, the occurrence of a kink or twist in the vicinity of a joined portion (joined surface) 6 between the first wire 2 and the second wire 3 when the guide wire 1 moves or rotates in the catheter.

The following materials are exemplified as the friction reduction materials: polyolefin such as polyethylene, polypropylene, or the like; polyvinyl chloride; polyester (PET, PBT, or the like); polyamide; polyimide; polyurethane; polystyrene; polycarbonate; silicone resin; fluorine-based resin (PTFE, ETFE, or the like); and a composite material which is a combination of these materials.

In particular, when fluorine-based resin (or a composite material containing fluorine-based resin) among these materials is used, it is possible to effectively reduce the friction resistance (slide resistance) between the guide wire 1 and the inner wall of the catheter, and thus it is possible to improve sliding performance, and the operability of the guide wire 1 in the catheter is further improved. Accordingly, it is possible to more reliably prevent the occurrence of a kink (bending) or twist of the guide wire 1, and particularly, the occurrence of a kink or twist in the vicinity of joined portions when the guide wire 1 moves and/or rotates in the catheter.

When fluorine-based resin (or a composite material containing fluorine-based resin) among these materials is used, the wire main body 10 can be coated with the resin material using baking, spraying, or the like in a state where the resin material is heated. Accordingly, adhesion between the wire main body 10 and the resin coating layer 8 is considerably good.

In a case where the resin coating layer 8 is made of silicone resin (or a composite material containing silicone resin), even if the resin coating layer 8 is not heated when the resin coating layer 8 is formed (the wire main body 10 is coated with the resin coating layer 8), it is possible to form the resin coating layer 8 that reliably and strongly adheres to the wire main body 10. That is, in a case where the resin coating layer 8 is made of silicon resin (or a composite material containing silicon resin), since a reaction curable resin material or the like can be used, the resin coating layer 8 can be formed at room temperature. Since the resin coating layer 8 is formed at room temperature, it is possible to simply perform coating, and to operate the guide wire in a state where sufficient joining strength of the joined portion 6 is maintained.

The thickness of the resin coating layer 8 is not limited to a specific dimension, and is appropriately determined while the purpose and the method of formation of the resin coating layer 8, the material of the resin coating layer 8, and the like are taken into consideration, and typically, the resin coating layer 8 preferably has a thickness (mean thickness) of approximately 1 µm to approximately 100 µm, and more preferably has a thickness of approximately 1 µm to approximately 30 µm. When the thickness of the resin coating layer 8 is excessively small, the purpose of formation of the resin coating layer 8 may not be sufficiently shown, and the separation of the resin coating layer 8 may occur, which are problems. When the thickness of the resin coating layer 8 is excessively large, physical characteristics of the wire main body 10 may be affected, and the separation of the resin coating layer 8 may occur, which are problems.

The resin coating layer 8 may be a single layer, or may be a laminated body with two or more layers.

Treatment (surface roughening, chemical treatment, heat treatment, or the like) can be applied to the outer circumferential surface (surface) of the wire main body 10 so as to improve adhesion of the resin coating layer 8, or an intermediate layer can be provided on the outer circumferential surface of the wire main body 10 so as to improve adhesion of the resin coating layer 8.

The outer surface of at least the distal end portion of the guide wire 1 is preferably coated with a hydrophilic material. In the embodiment, the outer circumferential surface (the outer surface) of the coil 4 of the guide wire 1 is coated with a hydrophilic lubricating layer 7 that is made of a hydrophilic material. Accordingly, lubricating performance is obtained due to wetness of the hydrophilic material, the friction (slide resistance) of the guide wire 1 is reduced, and the sliding properties are improved. As a result, the operability of the guide wire 1 is improved. In particular, since the curvature radius of an outer circumferential portion of the wire rod 40A in the constant outer-diameter/inner-diameter portion 41 is large, the outer surface of the hydrophilic lubricating layer 7 in the constant outer-diameter/inner-diameter portion 41 is formed as a substantially smooth outer surface. For this reason, a contact area between the constant outer-diameter/inner-diameter portion 41 and a vascular wall, the inner wall of the catheter, or the like increases, and lubricating performance is improved. Since the tapered portion 42, which is continuous with a proximal end side of the constant outer-diameter/inner-diameter portion 41, is formed by the circular wire rod 40B, the outer surface of the hydrophilic lubricating layer 7 of the tapered portion 42 is formed as a substantially wavelike outer surface. Accordingly, it is possible to push the guide wire 1 while safely widening the constricted portion when the guide wire 1 passes through a relatively narrow constricted portion.

The following materials are exemplified as the hydrophilic materials (the material of the hydrophilic lubricating layer 7): a cellulosic polymer, a polyethylene oxide polymer; a maleic anhydride polymer (for example, maleic anhydride copolymer such as methyl vinyl ether-maleic anhydride copolymer); an acrylamide polymer (for example, polyacrylamide, and polyglycidyl methacrylate-dimethyl acrylamide (PGMA-DMAA) block copolymer); water-soluable nylon; polyvinyl alcohol; polyvinylpyrrolidone; and the like.

In many cases, these hydrophilic materials show lubricating performance due to wetness (water absorption), and reduce friction resistance (slide resistance) between the guide wire 1 and the inner wall of the catheter in use therewith. Accordingly, the sliding performance of the guide wire 1 is improved, and the operability of the guide wire 1 in the catheter is further improved.

Hereinafter, a method of manufacturing the coil 4 will be described with reference to FIGS. 3 and 4. In FIGS. 3 and 4, the coil 4 is formed by grinding a coil member 400. Only the constant outer-diameter/inner-diameter portion 41 of the processed coil member 400 is illustrated.

First, as illustrated in FIG. 3, the coil member 400, which is made by helically winding a linear base material with a circular cross section, and a circular column-shaped grinding stone 100 are prepared. The material of abrasive grains of the grinding stone 100 is not limited to a specific material, and the following materials can be used: metallic oxides such as cerium oxide ($CeO_2$), manganese dioxide ($MnO_2$), aluminum oxides ($Al_2O_3$) (fumed alumina, colloidal alumina, and the like), and the like; silicon oxides ($SiO_2$) such as precipitated silica, fumed silica, colloidal silica, and the like; diamond; and the like.

Subsequently, a hard core member 200 is inserted into the coil member 400, and has an outer diameter (thickness) that is the same as or is slightly smaller than the inner diameter of the coil member 400.

Subsequently, the coil member 400 and the core member 200 rotate around the center axis 300 of the coil 4. At this time, the coil member 400 rotates in a clockwise direction when seen from the distal end side. The rotation speed of the coil member 400 preferably is 1.5 rps to 90 rps, and more preferably is 15 rps to 25 rps. The coil member 400 and the core member 200 may be rotated in a counter-clockwise direction.

Subsequently, the grinding stone 100 moves in a direction of arrow C in FIG. 4 (along a direction of the center axis 300 of the coil 4) while rotating around the center axis of the grinding stone 100. The grinding stone 100 rotates in a direction of arrow B in FIGS. 3 and 4. The grinding stone 100 may not move, and instead, the coil member 400 and the core member 200 may move in a direction opposite to the direction of arrow C in FIG. 4.

The rotation speed of the grinding stone 100 preferably is 10 rps to 1500 rps, and more preferably is 500 rps to 1000 rps. A movement speed V of each of the grinding stone 100, the coil member 400, and the core member 200 preferably 0.5 mm/s to 10.0 mm/s, and more preferably is 1.0 mm/s to 4.0 mm/s (refer to FIG. 3).

As illustrated in FIG. 4(*b*), a portion (through which the grinding stone 100 passes) of the coil member 400, that is, a grinding allowance 401, which is a part of the outer circumferential surface of the coil member 400, is ground and removed by the movement of the grinding stone 100. Since the grinding stone 100 rotates in the direction of arrow B in FIG. 3, the grinding allowance 401 is ground in an advance direction of the grinding stone 100. When the grinding is performed, the flat portion 45 and a burr 402 are formed on the outer circumferential surface of a portion (from which the grinding allowance 401 is removed) of the coil member 400.

The burr 402 is a portion that is not removed when the grinding allowance 401 is ground, and is formed close to the proximal end side. As described above, while moving toward the distal end side, the grinding stone 100 rotates such that the coil member 400 is ground in the advance direction, and thus the burr 402 protrudes in the advance direction (toward the proximal end side). The burr 402 works as the aforementioned protruding portion 46.

As such, the coil member 400 is ground in such a way that the burr 402 working as the protruding portion 46 is formed, and thus it is possible to easily obtain the coil 4 that can prevent the adjacent wire rods 40 from moving upward relative to each other.

Second Embodiment

FIG. 5 shows longitudinal sectional views illustrating a deformation process of a guide wire (a coil) in a second embodiment.

Hereinafter, the guide wire of the second embodiment will be described with reference to this drawing. The description will be centered around the points of difference between the first embodiment and the second embodiment, and the same items will not be described. For illustrative purposes, in FIG. 5, the right side and the left side are respectively referred to as a "proximal end" and a "distal end", and an upper side and a lower side are respectively referred to as the "top" and the "bottom".

This embodiment is the same as the first embodiment except that the cross-sectional shape of a wire rod 40A' is different from that in the first embodiment. Similar to the first embodiment, the wire rod 41B will be representatively described.

As illustrated in FIG. 5, the cross-sectional shape of the wire rod 41B has the flat portion 45, the curved portion 44, and a pair of the protruding portions 46. The pair of the protruding portions 46 is respectively provided on both ends of the curved portion 44, and specifically, is respectively provided at the boundaries between the curved portions 44 and the flat portions 45 on both ends. In a no-load state, the pair of the protruding portions 46 is respectively in contact with the protruding portion 46 of the wire rod 41A and the protruding portion 46 of the wire rod 41C.

As illustrated in FIG. 5(b), when the wire rod 41B moves upward relative to the wire rods 41A and 41C from an initial state illustrated in FIG. 5(a), an external force is reduced or released, and the wire rod 41B returns to its original position (no-load state) due to a restoring force of the wire rod 41B. At this time, the protruding portion 46 of the wire rod 41B slides against the outer circumferential surface of the protruding portion 46 of the wire rod 41A, the protruding portion 46 of the wire rod 41C slides against the protruding portion 46 of the wire rod 41B, and then the wire rod 41B can return its original state.

The wire rod 41B can easily return its original state from a state in which the wire rod 41B moves upward relative to the wire rods 41A and 41C (refer to FIG. 5(c)).

In the manufacturing of the wire rod 40A', the wire rod 40A' is ground from the proximal end side to the distal end side. In other words, the grinding stone 100 grinds the wire rod 40A' while moving in a direction opposite to the movement direction of the grinding stone 100 in the first embodiment. At this time, the grinding stone 100 rotates in a direction opposite to the rotation direction of the grinding stone 100 in the first embodiment. Accordingly, the burr 402 working as the protruding portion 46 is formed in the movement direction. As a result, it is possible to obtain the wire rod 40A' with a pair of the protruding portions 46.

The coil and the wire guide have been described based on the illustrated embodiments; however, the present invention is not limited to those in the embodiments, and configurational elements can be replaced with arbitrary elements having the same functions. Other arbitrary configurational elements may be added to the present invention.

In the embodiments, the protruding portion is provided at the boundary between the curved portion and the flat portion; however, the present invention is not limited to the configuration in the embodiments, and the protruding portion may be provided in the vicinity of the boundary.

In the embodiments, the coil member is ground; however, the present invention is not limited to the processing method in the embodiments, and the coil member may be cut.

When the coil member is processed, the grinding stone may grind the grinding allowance little by little while moving multiple times.

A coil of the present invention is a coil that is made by helically winding a wire rod, and a cross-sectional shape of the wire rod has a curved portion that is arcuately curved toward the center axis of the coil; a flat portion that is provided on an outer circumference of the coil, and is formed in a flat shape with a curvature that is smaller than that of the curved portion; and at least one protruding portion that is provided at the boundary between the curved portion and the flat portion or in the vicinity of the boundary, and protrudes toward an adjacent the wire rod.

According to the present invention, it is possible to reliably prevent the adjacent wire rods from being stuck to each other, and to prevent the occurrence of a state in which the adjacent wire rods move upward relative to each other and remain as it is, and to obtain the coil and a guide wire with good operability.

In particular, since the cross-sectional shape of the wire rod of the coil has the protruding portion that protrudes toward the adjacent wire rod, even if one wire rod of the adjacent wire rods moves upward relative to the other wire rod, the one wire rod can return to a no-load state while sliding against the protruding portion of the other wire rod. Accordingly, it is possible to prevent the guide wire from bulging, and to prevent an increase in friction resistance associated with the bulging of the guide wire, and it is possible to reliably transmit a pushing force and a rotating force to the distal end of the guide wire, that is, the operability of the guide wire is improved.

As a result, the coil, the guide wire, and the method of manufacturing the guide wire can be industrially applied.

The detailed description above describes a coil, a guide wire, and a method of manufacturing the coil. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST

1: guide wire
10: wire main body
2: first wire
21: foremost end portion
22, 24: tapered portion
23, 25: constant outer-diameter portion
3: second wire
4: coil
40, 40A, 40A', 40B, 41A, 41B, 41C: wire rod
41, 43: constant outer-diameter/inner-diameter portion
42: tapered portion
44: curved portion
45: flat portion
46: protruding portion
51 to 53: fixing material
6: joined portion
7: hydrophilic lubricating layer
8: resin coating layer
100: grinding stone
200: core member
300: center axis
400: coil member
401: grinding allowance
402: burr
R1, R2, R3: curvature
V: movement speed

What is claimed is:
1. A coil that is made by helically winding a wire rod, wherein a cross-sectional shape of the wire rod includes:
a curved portion that is arcuately curved toward a center axis of the coil;
a flat portion that is provided on an outer circumference of the coil, and is formed in a flat shape with a curvature that is smaller than that of the curved portion; and
at least one protruding portion that is provided adjacent an end of the flat portion and protrudes from a convex surface of the curved portion toward a proximally adjacent wire rod, a convex surface of the protruding portion intersecting with convex surface of the curved portion to define a recess,
wherein in a no-load state in which an external force is not applied, only the convex surface of the protruding portion, including a proximalmost tip of the convex surface of the protruding portion, is in contact with the proximally adjacent wire rod, the convex surface of the curved portion is not in contact with the proximally adjacent wire rod, and the recess is not in contact with the proximally adjacent wire rod.

2. The coil according to claim 1,
wherein the convex surface of the protruding portion is curved with a curvature greater than that of the curved portion.

3. The coil according to claim 1,
wherein when an external force is applied such that contact pressure between adjacent wire rods increases, one wire rod of the adjacent wire rods moves upward relative to an other wire rod, and when the external force is reduced or released, due to the resilience of the one wire rod, the one wire rod returns to an original position thereof while the curved portion of the one wire rod slides against the protruding portion of the other wire rod.

4. The coil according to claim 2,
wherein when an external force is applied such that contact pressure between adjacent wire rods increases, one wire rod of the adjacent wire rods moves upward relative to an other wire rod, and when the external force is reduced or released, due to the resilience of the one wire rod, the one wire rod returns to an original position thereof while the curved portion of the one wire rod slides against the protruding portion of the other wire rod.

5. The coil according to claim 1,
wherein protruding portions are respectively provided adjacent both respective ends of the flat portion.

6. The coil according to claim 2,
wherein protruding portions are respectively provided adjacent both respective ends of the flat portion.

7. A guide wire comprising:
the coil according to claim 1; and
a wire main body that has flexibility,
wherein the wire main body is inserted into the coil.

8. The coil according to claim 1, wherein, in the no-load state, the proximalmost tip of the convex surface of the protruding portion is in contact with a distal end portion of the convex surface of the curved portion of the proximally adjacent wire rod.

9. The coil according to claim 1, wherein, a radius of curvature of the curved portion is greater than a radius of curvature of the protruding portion.

10. The coil according to claim 9, wherein, in the no-load state, the proximalmost tip of the convex surface of the protruding portion is in contact with a distal end portion of the convex surface of the curved portion of the proximally adjacent wire rod.

11. The coil according to claim 1, wherein, in the no-load state, the proximalmost tip of the convex surface of the protruding portion is in contact with a distalmost tip of a convex surface of a second protruding portion of the proximally adjacent wire rod.

* * * * *